United States Patent [19]

Berlin et al.

[11] 3,987,055

[45] Oct. 19, 1976

[54] AZASTEROIDS COMPOUNDS AND DERIVATIVES

[75] Inventors: Kenneth Darrell Berlin; Norman Nevill Durham, both of Stillwater, Okla.; Claude Desjardins, Austin, Tex.

[73] Assignee: The Board of Regents for the Oklahoma Agricultural & Mechanical Colleges acting for and on behalf of Oklahoma State University of Agriculture and Applied Science, Stillwater, Okla.

[22] Filed: Sept. 11, 1974

[21] Appl. No.: 505,136

Related U.S. Application Data

[63] Continuation-in-part of Ser. No. 225,593, Feb. 11, 1972, abandoned.

[52] U.S. Cl. .................. 260/310 R; 260/310 C; 260/310 D; 260/310 A; 424/273
[51] Int. Cl.² ............................................ C07D 231/56
[58] Field of Search .......... 260/310 R, 310 D, 310C

[56] References Cited
OTHER PUBLICATIONS

Morgan et al., J. Heterocyclic Chemistry, 1971, 8(1), pp. 61–63.
Chesnut et al., Can. J. Biochem., 1972, 50(5), pp. 516–523.

*Primary Examiner*—Donald B. Moyer
*Attorney, Agent, or Firm*—Head, Johnson & Chafin

[57] ABSTRACT

Azasteroids and certain derivatives each of a five ring system containing at least one aromatic nucleus and at least one nitrogen atom. The ring system is fused to a tetrahydrotetralin system or a tetrahydrophenanthrene system. The compounds have solubility in water and disclose antimicrobial, antifertility and potentate the activity of antibiotics and certain anticancer agents.

6 Claims, No Drawings

AZASTEROIDS COMPOUNDS AND DERIVATIVES

This is a continuation-in-part of our copending application U.S. Ser. No. 225,593, filed Feb. 11, 1972 now abandoned, entitled AZASTEROIDS COMPOUNDS AND DERIVATIVES.

This invention relates to azasteroids, certain derivatives thereof and model compounds which contain at least one aromatic nucleus and at least one nitrogen atom in a 5-membered ring.

The novel compositions of this invention are represented by the following general structural formula

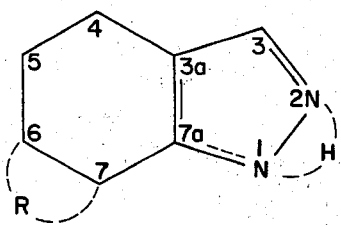

wherein R represents the carbon and hydrogen atoms necessary to complete one of the following structures:

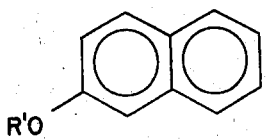

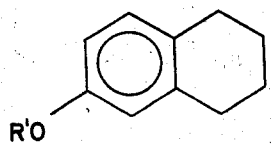

or

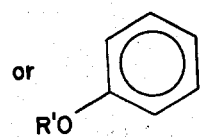

in which R' may be H, $CH_3$, $C_2H_5$ or $C_3H_7$. The bridgehead* carbon atom 3a may be unsubstituted or it may be substituted by H or $CH_3$ in which case the only double bond in the pyrazole ring is represented by the dashed line and the unsatisfied valences of carbon 3 are satisfied by two hydrogen atoms or oxygen, however, when the free valence of carbon 3 is satisfied by oxygen, the labile hydrogen must be attached to the number 2 nitrogen in the pyrazole ring and when the free valence of carbon 3 is satisfied by hydrogen, the labile hydrogen atom is attached to the number one nitrogen of the pyrazole ring. and H is a labile hydrogen atom attached to one of two nitrogen atoms of the pyrazole ring. It should be pointed out that the compounds of this invention exist in tautomeric forms, one form predominating when the bridgehead carbon atom is substituted and the other tautomer predominating when said carbon atom is unsubstituted.

* A bridge is a valence bond or atom connecting two different parts of a molecule. The two tertiary carbon atoms connected through the bridge are termed "bridgeheads".

Classes of compounds included by the above general structural formula are:

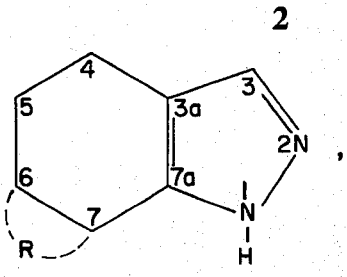

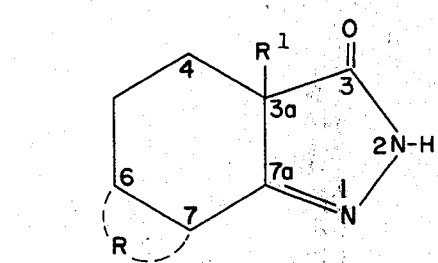

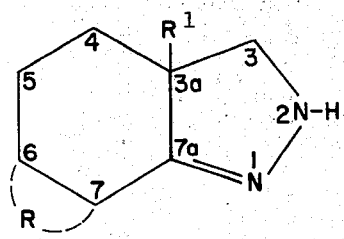

The substituent R in these formulas is identical to the values assigned R in the general formula first above written. $R^1$ may be either H or $CH_3$.

Subgeneric groups coming under the above structural formula are:

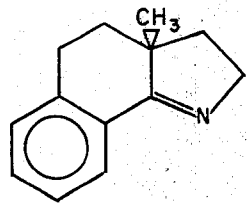

COMPOUND 1

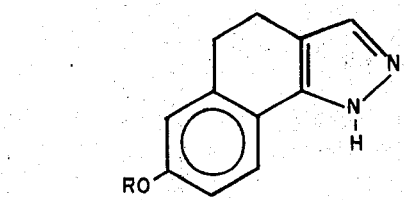

COMPOUND 2

R = H, $CH_3$, $C_2H_5$ or $C_3H_7$

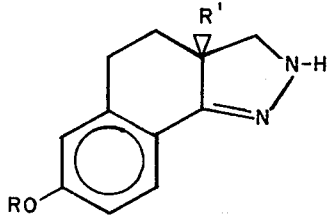

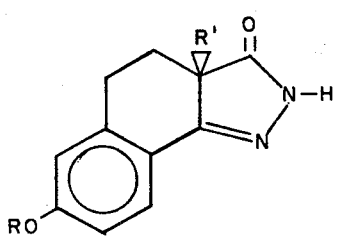

| COMPOUNDS 3 | COMPOUNDS 4 |
|---|---|
| a. R=H, R'=H | a. R=H, R'=H |
| b. R=CH$_3$, R'=H | b. R=CH$_3$, R'=H |
| c. R=H, R'=CH$_3$ | c. R=H, R'=CH$_3$ |
| d. R=CH$_3$, R'=CH$_3$ | d. R=CH$_3$, R'=CH$_3$ |
| e. R=C$_2$H$_5$ or C$_3$H$_7$, R'=H or CH$_3$ | e. R=C$_2$H$_5$ or C$_3$H$_7$, R'=H or CH$_3$ |

| COMPOUNDS 5 | COMPOUNDS 6 |
|---|---|
| a. R=H, R'=H | a. R=H, R'=H |
| b. R=CH$_3$, R'=H | b. R=CH$_3$, R'=H |
| c. R=H, R'=CH$_3$ | c. R=H, R'=CH$_3$ |
| d. R=CH$_3$, R'=CH$_3$ | d. R=CH$_3$, R'=CH$_3$ |
| e. R=C$_2$H$_5$ or C$_3$H$_7$, R'=H or CH$_3$ | e. R=C$_2$H$_5$ or C$_3$H$_7$, R'=H or CH$_3$ |

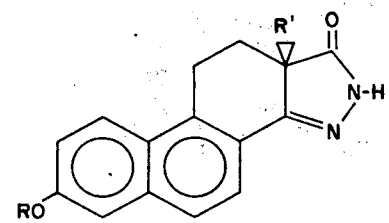

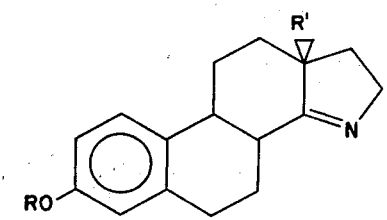

| COMPOUNDS 7 | COMPOUNDS 8 |
|---|---|
| a. R=H, R'=H | a. R=H, R'=H |
| b. R'CH$_3$, R'=H | b. R=CH$_3$, R'=H |
| c. R=H, R'=CH$_3$ | d. R=H, R'=CH$_3$ |
| d. R=CH$_3$, R'=CH$_3$ | d. R=CH$_3$, R'=CH$_3$ |
| e. R=C$_2$H$_5$ or C$_3$H$_7$, R'=H or CH$_3$ | e. R=C$_2$H$_5$ or C$_3$H$_7$, R'=H or CH$_3$ |

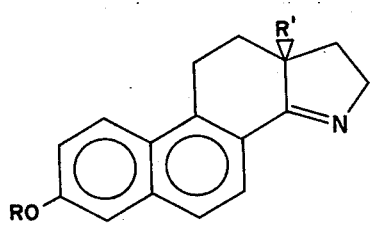

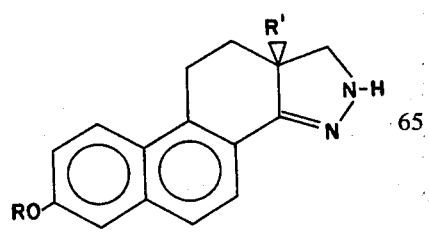

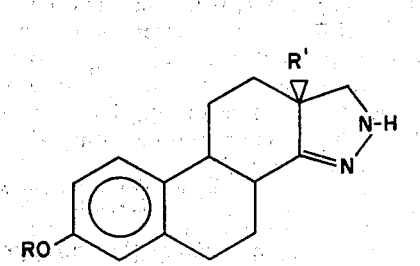

continued

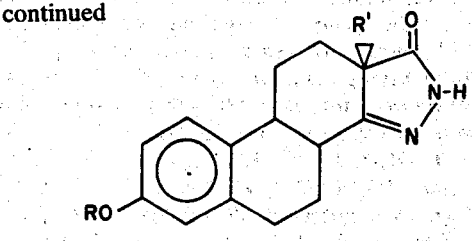

| COMPOUNDS 9 | COMPOUNDS 10 |
|---|---|
| a. R=H, R'=H | a. R=H, R'=H |
| b. R=CH₃, R'=H | b. R=CH₃, R'=H |
| c. R=H, R'=CH₃ | c. R=H, R'=CH₃ |
| d. R=CH₃, R'=CH₃ | d. R=CH₃, R'=CH₃ |
| e. R=C₂H₅ or C₃H₇, R'=H or CH₃ | e. R=C₂H₅ or C₃H₇, R'=H or CH₃ |

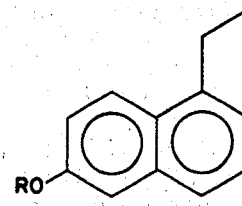

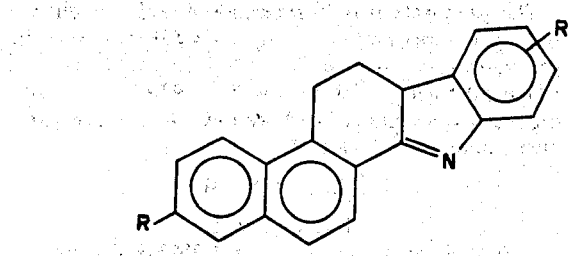

| COMPOUNDS 11 | COMPOUNDS 12 |
|---|---|
| a. R=H | a. R=H, R'=H |
| b. R=CH₃ | b. R=OH, R'=H |
| | c. R=OCH₃, R'=H |
| | d. R=OC₂H₅ or OC₃H₇, R'=H |
| | e. R=OCH₃, R'=F, Cl, Br |

BACKGROUND OF THE INVENTION

Steroid nuclei containing nitrogen have been shown to possess a wide range of physiological activities. The vast majority of these azasteroids are derived by modification of naturally occurring steroids.

Of the known azasteroids (3,2-c)-2'-phenylpyrazole of 9α-fluoro-6,16α-dimethyl-Δ⁶-hydrocortisone is claimed to be he most potent anti-inflammatory steroid known—over 2000 times as powerful as hydrocortisone itself. The 0-methyl ether of 16-azaestrone has exhibited significant hypocholesterolemic activity but possesses less than 1.01% of the estrogenic activity of the parent estrone. 4-Dimethylaminoethyl-4-aza-5-cholesten-3-one methiodide has been shown to irreversibly inhibit the growth of *Bacillus subtilis* cultures at concentrations as low as 1 μg/ml. 17-Hydroxy-17 α-methylandrostano[3,2]-μ pyrazole exhibits an anti-ovulatory activity one-fifth of that observed for norethisterone when administered orally in rats.

Monoazasteroids were first synthesized in the 1930's as a "synthetic decarboxylase." Some of the known azasteroids are derivatives of 4,4-dimethyl-5-αandrost-14-ene and are intermediates in steroid-terpene structure correlations. It is apparent that the 15,16-diazasteroids, and especially the 15-monoazasteroids have been little studied, despite the fact that this latter class of compounds combines the steroid nucleus with the often biologically active indole nucleus in a single structure.

METHODS OF PREPARATION

The preparation of compounds 5,6,8 and 9 require first the preparation of an intermediate compound, 1,2,3,4-tetrahydro-7-methoxy-2-methyl-1-oxo-2-phenanthrenepropionic acid. The precursor of this acid, the known ketone 3,4-dihydro-7-methoxy-2-methyl-1(2H)-phenanthrone, in the quantity of 2.8 grams, 0.0182 mol., was placed in a 250-ml round-bottom flask (fitted with an addition funnel and a $N_2$ inlet) and was dissolved in 100 ml of warm (60° C) tert-butyl alcohol containing 0.2g of aqueous 40% KOH. The ketone was only sparingly soluble in the alcohol and the reaction mixture had to be maintained at around 60° C to effect solution.

Acrylonitrile (0.62 g, 0.0182 mol), bp 75°–78° C, dissolved in 10 ml of tert-butyl alcohol, was added dropwise over a 30 minute period. The reaction mixture was stirred overnight at 60° C under $N_2$. The solvent was then removed by an aspirator, and the residue was boiled 36 hours with 50 ml of aqueous 20% KOH. The reaction mixture was then diluted with $H_2O$, extracted two times with ether, and neutralized with dilute HCl. The resulting precipitate was washed with $H_2O$ and air-dried to yield 3.3 g of dark-brown solid which was crude acid. This material was washed through a 10 × 1 silica gel (35g) column with hot benzene and recrystallized twice from 150 ml of benzene to yield 2.0 g (56.5%) of white, crystalline acid, (mp 157.5°–159° C); $v_{max}^{KBr}$ 1680 (acid C=O) and 1655 cm⁻¹ (ketone C=O); nmr (10% in $DCCl_3$) 1.22 (s, 3 H, $CH_3$), 1.76–2.67 (m, 6 H, aliphatic $CH_2$), 3.13–3.47 (bt, 2 H, benzylic $CH_2$), 3.90 (s, 3 H, $OCH_3$), 7.00–8.20 (m, 5 H, aromatic H), and 11.41 (s, 1 H, $CO_2H$).

Calculations for $C_{19}H_{20}O_4$ disclosed: C, 73.06; H, 6.45. Analysis found: C, 73.20; H, 6.31.

The above procedure was performed successfully on ten times the above scale. When the condensation was attempted in 1,4-dioxane using Triton B (benzyltrimethylammonium hydroxide) as a catalyst, the yield of 1,2,3,4-tetrahydro-7-methoxy-2-methyl-1-oxo-2-phenanthrenepropionic acid was only 49% and the phenanthrone recovered was unchanged in the amount of 32%.

EXAMPLE I

PREPARATION OF COMPOUNDS 5

The phenanthronepropionic acid (23 g, 0.076 mol, mp 155°–157.5° C) was dissolved in 500 ml of anhydrous, reagent grade acetone in a 1-l., three-necked, round-bottom flask equipped with a thermometer, $N_2$ inlet, and addition funnel with $CaSO_4$ drying tube. The mixture was cooled to −5° C in a salt-ice bath and 12.2 g (0.122 mol) of triethylamine was added dropwise, the temperature being kept below 0° C. Ethyl chloroformate (4.7g, 0.122 mol,) was then added with the temperature at 0° C.

The mixture was stirred in the cold for 30 minutes and 10.3 g (0.16 mol) of $NaN_3$ in 40 ml of $H_2O$ was added dropwise, again at 0° C. The mixture was stirred at 0° C for 1 hr and poured into ice water.

A crystalline crude azide that separated amounted to 18.0 g and decomposed with partial melting at 90°–100° C (sealed tube under vacuum). The azide was dissolved in 500 ml of toluene and heated on a steam bath until gas evolution ceased (1–2 hr). Toluene was removed in vacuo; the residue amounted to 16.0 g of crude isocyanate which was heated at reflux for 24 hr with 300 ml of 1:1:1 $H_2O$-glacial acetic acid-concentrated HCl. The mixture was cooled, diluted ($H_2O$), extracted 3 times (ether), filtered, and then neutralized (aqueous 10% $NaHCO_3$).

The resulting yellow solid (9.0 g), which had a very broad melting range (120°–200° C), was warmed (50°–60° C) with 150 ml of benzene, and the mixture was filtered. The residue was again extracted with an additional 150 ml of benzene. The filtrates were combined and reduced to 150-ml total volume by boiling on a hot plate. Cooling the solution to room temperature caused it to deposit a small additional quantity of material. This solution was then filtered and the benzene-insoluble residues (crude compound 5c) were combined and set aside.

The yellow benzene solution was passed over a 15 × 1 cm column of neutral alumina (50 g) and the column was washed with additional benzene until no further material was eluted. The colorless benzene eluate was evaporated to dryness under aspirator vacuum. The white, amorphous residue was crystallized from acetone and then sublimed at 150° C (0.04 mm) to yield 5.0 g of compound 5d (1,10,11,11a-tetrahydro-7-methoxy-11a-methyl-2H-naphth[1,2-g]indole) mp 180°–181° C (st, under vacuum); molecular weight by mass spectral analysis in 265 (calculated for $C_{18}H_{19}NO$, 265.34); $v_{max}^{KBr}$ 1600 cm$^{-1}$ (C=N); nmr (10% in $DCCl_3$) 1.11 (s, 3 H, $CH_3$) 1.65–2.50 (m, 4H, aliphatic $CH_2$), 2.94–3.47 (m, 2 H, benzylic $CH_2$), 3.78–4.25 (m, C=NCH$_2$) and 3.90 (s, OCH$_3$) (total 5 H), and 7.06–8.27 (m, 5 H, aromatic H).

The calculated analysis for $C_{18}H_{19}NO$ was C, 81.47; H, 7.22; N, 5.28. The analysis found was C, 81.70; H, 7.30; N, 5.29.

The insoluble residue from the benzene extraction was dissolved in 800 ml of warm (50°–60° C), aqueous 2.5% NaOH. The NaOH solution was cooled and filtered to remove a very small quantity of insoluble residue. The solution was then made acid with dilute HCl, the acidified solution being held near 40° C to prevent crystallization of what was apparently a sparingly soluble hydrochloride. The warm, acid solution was neutralized with aqueous 10% $NaHCO_3$, and the precipitated solid was sublimed at 250° C (0.04 mm) to yield 2.5 g of light yellow, crystalline compound 5c (1,10,11,11a-tetrahydro-11a-methyl-2H-naphth[1,2-g]indol-7-ol) having a melting point of 287°–290° C, with apparent decomposition (st, under vacuum); molecular weight by mass spectral analysis is 251 (calculated for $C_{17}H_{17}NO$, 251.32); $v_{max}^{KBr}$ 1600 cm$^{-1}$ (C=N); nmr (5% in $C_5D_5N$) 1.00 (s, 3 H, $CH_3$), 1.33–233 (m, 4 H, aliphatic $CH_2$), 2.96–3.46 (m, 2 H, benzylic $CH_2$), 3.68–4.49 (m, 2 H, C=NCH$_2$), 7.10–8.90 (m, 5 H, aromatic H), and 11.5–12.5 (b, 1 H, aromatic OH). The calculated analysis for $C_{17}H_{17}NO$ was: N, 5.62. The analysis found was N, 5.76.

Compound 5d (4.0 g, 0.015 mol) was boiled for 12 hr under $N_2$ with 50 ml of 48% HBr. The mixture was cooled and filtered through a glass-fritted funnel and the solid isolated was dissolved in 1 liter of warm (50° C) aqueous 2% NaOH. The basic solution was filtered and neutralized with dilute HCl (pH 6.5 to<7). The resulting solution was made basic with excess aqueous 10% $NaHCO_3$. The solid thus obtained was filtered, vacuum-dried, and sublimed at 250° C (0.04 mm) to yield 2.9 g of the compound 5c identical with the material described above.

The preparation of compounds 5a, 5b and 5e can be accomplished using similar techniques to those described above to prepare compounds 5c and 5d. Following the procedure above but substituting 3,4-dihydro-7-methoxy-(or ethoxy or propoxy)-1-oxo-2-phenanthrenepropionic acid for 3,4-dihydro-2-methyl-1-oxo-2-phenanthrenepropionic acid, one can obtain 5a and 5b (or 5e).

The preparation of compounds 8 and 9 begin with the compound 1-keto-1,2,3,4,9,10-hexahydrophenanthrene disclosed in the *Journal of American Chemical Society*, Volume 64, Page 979, 1942, following techniques similar to those described above to prepare compounds 5c and 5d.

EXAMPLE II

Preparation of 3,3a,4,5-Tetrahydro-3a-methyl-2H-benz[g]indole Compound 1

1-Tetralone (24.5 g, 0.168 mol) was converted to 27.3 g (92%) of the known crude hydroxymethylene compound essentially by the method reported in the literature [*Journal of American Chemical Society*, 66, 218 (1944) and *Bull. Soc. Chim. France*, 556 (1958)].

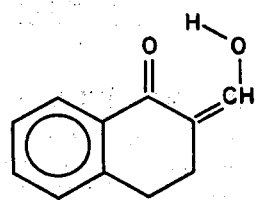

The crude product was condensed with 1-butanethiol in the presence of p-toluenesulfonic acid to give a quantitative yield of crude 2-(n-butylthiomethylene)-1-tetralone. The crude thioether (21.6 g, 0.088 mol) in aqueous base (≈3:1, $H_2O$:NaOH was reductively desulfurized employing deactivated Raney nickel in an open beaker at 75° C for 1 hour.

The yield of 2-methyl-1-tetralone was 17 g (94%), identical with authentic material by comparative glpc analysis. The 2-methyl-1-tetralone was converted in 98% yield to 1,2,3,4-tetrahydro-2-methyl-1-oxo-2-naphthalenepropionic acid (crude) by the method described earlier for the preparation of the phenanthrenepropionic acid.

The crude naphthalenepropionic acid (a viscous yellow oil) was converted to the benzindole (Compound 1) by the same method described earlier for the preparation of the compound 5d. Compound 1 was produced from the acid in 45% yield as a water-white liquid: bp 84°–87° C (0.04 mm); homogenous by glpc analysis; $v_{max}^{KBr}$ 1620 cm$^{-1}$ (C=N); nmr (neat) 0.88 (s, 3 H, CH$_3$), 1.15–2.17 (m, 4 H, aliphatic CH$_2$), 2.20–3.15 (m, 2 H, benzylic CH$_2$), 3.50–4.20 (m, 2 H, C=NCH$_2$), 6.76–7.23 (m, 3H, aromatic H), and 7.88–8.22 (m, 1 H, aromatic H with ortho keto function). The analysis of this material was calculated for C$_{13}$H$_{15}$N was: N, 7.56; the analysis found was: N, 7.73.

EXAMPLE III

Preparation of
10,11-Dihydro-7-methoxy-3H-naphth[1,2-g]indazole
Compound 11b

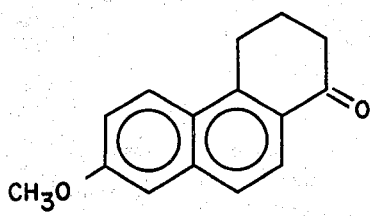

(3.5 g., 0.0154 mole) was added to a stirred mixture of 1.7 g. (0.0315 mole) of sodium methoxide, 2.3 g. (0.0312 mole) of ethyl formate and 50 ml. of benzene under nitrogen in a 100 ml, round bottom flask.

The mixture was stirred for 6 hours and then poured into one liter of ice water; the resulting mixture was extracted with 300 ml. of ether. The organic phase was washed with 500 ml. of aqueous 5% sodium hydroxide; the aqueous extracts were combined, and the combined extracts were acidified with excess concentrated hydrochloric acid. The precipitated solid material was filtered out and vacuum-dried to yield 2.8 g. (72%) of 3,4-dihydro-2-(hydroxymethylene)-7-methoxy-1(2h)-phenanthrone as a yellow powder. This material (2.8 g., 0.011 mole) was dissolved in 300 ml. of methanol, and 3 ml. of 95% hydrazine was added. The solution was stirred 4 hours and then reduced to 50 ml. in volume by boiling on a hot plate. Upon cooling, 1.7 g. of the compound 11b separated as feathery, yellow needles (softened at 190° C, m.p. 212°–213° C, s.t., vac.). This material was recrystallized from 200 ml. of benzene, yielding 1.1 g. of compound 11b as a white powder (m.p. 212.5°–2.14°, s.t., vac.); uv λ max (ethanol) 266.5 mμ (log.=4.537); nmr (perdeuteriopyridine) δ2.76–3.57 (m, 4H, CH$_2$), 3.81 (s, 3H, OCH$_3$), 7.17–8.85 (m, 6H, aromatic and vinyl H), and 13.5–14.9 (b, 1H, NH).

The analysis of this compound was calculated for C$_{16}$H$_{14}$N$_2$O as follows: C, 76.78: H, 5.64; N, 11.19 and was found to be C, 76.88; H, 5.75; N, 11.02.

EXAMPLE IV

Preparation of
10,11-Dihydro-3H-naphth[1,2-g]indazol-7-ol
Compound 11a.

The methyl ether compound 11b (0.50 g.,0.0020 mole) was boiled with 25 ml. of aqueous 48% hydrobromic acid for 12 hours under nitrogen purge. The mixture was cooled, made strongly alkaline with aqueous 10% sodium hydroxide and filtered. The alkaline filtrate was neutralized with dilute HCl (pH 6.5 to < 7). The resulting solution was treated with aqueous 10% sodium bicarbonate solution and the resulting gray precipitate was filtered and sublimed at 240° C/0.03 mm. to yield 0.4 g. (85% of compound 11a as a light orange crystalline solid (m.p. 258°–261° C,s.t., vac.; uv λmax (sodium salt in water) 257.5 mμ (log = 4.594); nmr (perdeuteriopyridine)δ2.70–3.59 (m, 4H, CH$_2$), 7.16–8.82 (m, 6H, aromatic and vinyl H), and 12.1–14.1 (b, 2H, OH and NH). The indazolol compound 11a (0.2 g.) was recrystallized from 1:1:1: mixture of pyridine: benzene:cyclohexane and then sublimed again as above to yield 0.15 g. of a white, crystalline solid, m.p. unchanged. An analysis of this material was calculated for C$_{15}$H$_{12}$N$_2$O as follows: C, 76.25; H, 5.12; N, 11.86 and was found to be C, 76.52; H, 5.26; N, 12.00.

EXAMPLE V

Preparation of 4,5-Dihydro-1H-benz[g]indazol-7-ol
Compound 2

4,5-Dihydro-7-methoxy-1H-benz[g]indazol was prepared by a method known in the art. This compound, (10.0 g., 0.0500 mole, m.p. 162°–163.5° C), was boiled with 250 ml of aqueous 48% hydrobromic acid for 12 hours under nitrogen purge. The mixture was cooled and filtered, and the resulting pink solid was dissolved in 200 ml. of aqueous 6% sodium hydroxide. The alkaline solution was filtered and neutralized with dilute HCl (pH 6.5 to <7). Treatment with 10% sodium bicarbonate solution yielded 6.8 g. (73%) of an off-white powder, compound 2 (m.p. 198°–203° C, s.t., vac.).

An analytical sample of compound 2 was recrystallized from acetonitrile and sublimed (180°/0.03 mm.), to yield a white, hard, microcrystalline solid (m.p. 206.5°–208° C s.t., vac);uv λmax (water) 270 mμ (logε = 4.196); nmr (perdeuteriopyridine) δ2.78 (bs, 4H, CH$_2$), 6.78–8.12 (m, 4H, aromatic and vinyl H), and 12.4 (bs, 2H, OH and NH). An analysis of this material was calculated for C$_{11}$H$_{10}$N$_2$O as follows: C, 70.95, H, 5.41; N, 15.05 and was found to be C, 70.85; H, 5.37; N, 14.81.

Compounds 6 are prepared using similar techniques to those described for the preparation of compound 2, except that the starting material is 3,4-dihydro-7-methoxy-2-methyl-1(2H)phenanthrone.

Compounds 3 are prepared using similar techniques to those described for the preparation of compound 2, except that the starting material is 6-methoxy-1-tetralone.

EXAMPLE VI

Preparation of Compounds 4c and 4d.

6-Methyoxytetralone (68.2 g, 0.328 mole), dimethyl carbonate (416 ml, 0.448 mole), and sodium methoxide (24.2 g, 0.448 mole) were placed in a 1000 ml flask. The mixture was heated at reflux for 2.5 hours and allowed to cool. Methanol (200 ml) was added to dissolve the precipitate and an additional 200 ml. of methanol and 91.4 g (0.644 mole) of methyl iodide were added. The mixture was stirred overnight at room temperature.

The solution was brought to a boil and neutralized (2N acetic acid). The volume of solution was reduced by distillation by about one-half. Upon cooling, crystals of the following keto ester compound precipitated:

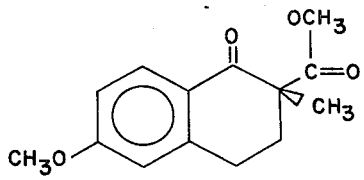

The yield was 82% (54.0 g) based upon 6-methoxytetralone. The melting point was 91.5°–92.5° C (s.t.) which was in agreement with a literature value for the compound prepared by a known method.

The ketoester compound (14.8 g, 0.059 mole) and hydrazine (19.2 g, 0.60 mole) were stirred in a flask under $N_2$ at room temperature for 4 hours. Absolute methanol was added to keep the mixture fluid along with 5 g of hydrazine.

Water (200 ml) was then added and the mixture was stirred for 0.75 hours. The mixture was then filtered, and the residue was washed (100 ml of water) three times. The white, solid compound 4d was vacuum-dried at 50° C; yield 12.29 g (90.5%) m.p. 217.5°–218.5°.

An analysis of this material was calculated for $C_{13}H_{14}N_2O$ as follows: C, 67.81; H, 6.12; N, 12.17; and was found to be: C, 67.69; H, 6.22, N, 12.34.

Treatment of compound 4d with 48% HBr as described previously for conversion of compound 5d to 5c gave crude compound 4c which was dissolved in 6% NaOH and heated over activated charcoal. The solution was filtered and neutralized (50% aq. acetic acid) and allowed to cool. A fine precipitate of compound 4c formed. An analysis of this material was calculated for $C_{12}H_{12}N_2O_2$ as follows: C, 66.66, H, 5.55; N, 12.96 and was found to be: C. 66.29; H, 5.59; N, 12.63.

Compounds 4a, 4b, 4e and 4f are prepared in similar fashion. Compounds 7 are prepared using the same techniques as compounds 4e and 4d, except that the starting material is 3,4-dihydro-7-methoxy-2-methyl-1(2H)-phenanthrone. Compounds 10 are prepared using the same techniques as compounds 4c and 4d, except that the starting material is 1-keto-1,2,3,4,9,10-hexahydrophenanthrene.

Compound 12 may be prepared using techniques similar to those employed in preparation of compound 2, starting with the same phenantrane compound used as a starting material for the production of compound 11b. For further information on the general techniques used in the preparation of compound 12, reference may be made to *Proceding of Oklahoma Academy of Science*, Volume 47, Page 215, 1966 issue, published in 1968.

EXAMPLE VII

Preparation of 2,10,11,11a-tetrahydro-7-methoxy-11a-methyl-1H-phenanthro[1,2-c]-pyrazol-1-one Compound 7d The known phenanthrone

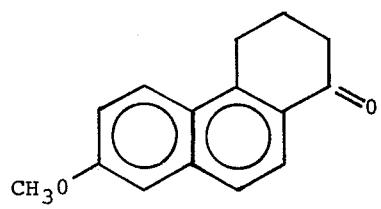

(1.75 g, 0.0078 mole) and a large excess of dimethyl carbonate (45 ml, 0.534 mole) were stirred together for 5 minutes in a 200 ml round bottom flask equipped as usual. Sodium methoxide (0.484 g, 6.0089 mole) was added and the solution was heated to a boil (the color turned red to dark red in 15 minutes.). A reddish precipitate appeared in 15 minutes, and heating was stopped. After stirring for 15 minutes the mixture attained room temperature and 30 ml of $CH_3OH$ (absolute) was added. The precipitate dissolved. Methyl iodide (0.852 g, 0.006 mole) was added and the resulting mixture was stirred overnight at room temperature.

One ml of $CH_3I$ was added and the mixture was heated gently for 5 minutes and then cooled to room temperature. The mixture was acidified with 2N acetic acid, (pH 6.7) evaporated to about ⅓ volume, and cooled in a refrigerator. A tarry substance precipitated; it was washed with water and then extracted (2 times) with ether. The extracts were washed with $H_2O$ and finally with saturated NaCl solution. The solution was dried ($MgSO_4$) and filtered. Evaporation of the ether gave an oil which was used immediately. It was presumed to be crude keto ester:

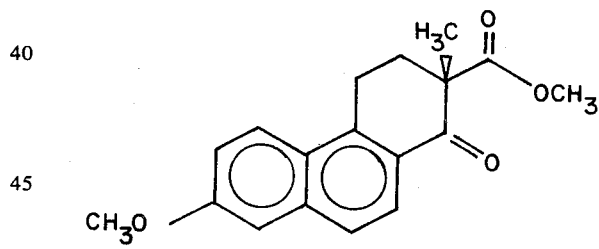

This compound was dissolved in 30 ml. of absolute $CH_3OH$ (under $N_2$) and 6 g (0.187 mols) of hydrazine (95%, Eastman Kodak) was added. The color changed to orange and a yellow solid formed after 3 hours of stirring without heating. Water was added (75 ml) a the resulting mixture stirred for an additional 2 to 5 hours. Crystals formed and were filtered. Sublimation gave 1.54 g (73% of compound 7d), m.p. 258°–260° C. $v_{max}{}^{KBr}$ 1690 cm$^{-1}$ (C=O).

The calculated analysis for $C_{17}H_{16}N_2O_2$ was C, 72.86; H, 5.71; N. 16.00. The analysis found was C, 72.73; H, 5.62; N, 9.86.

PROPERTIES OF THE COMPOUNDS

We now wish to describe valuable properties of these members of the azasteroid family and related, simple model systems. These compounds have shown antimicrobial activity, antifertility activity, anticancer activity and potentiate the activity of antibiotics and certain anticancer agents.

The hydroxybenzindazole (compound 2) delayed (inhibited) the initiation of growth of selected unrelated bacteria when incorporated in the growth medium. The inhibition was dependent on the concentration of the test compound and the nature of the organism. Bacillus subtilis W23 and Escherichia coli B were sensitive to 86 µg/ml as indicated by the increased lag (approximately 3 hours) in the initiation of growth with only slight inhibition observed in the lower concentration (46 µg/ml). Pseudomonas fluorescens NND was not sensitive to the hydroxybenzindazole in the concentrations tested.

The influence of cell mass on the antimicrobial potential of the hydroxybenzindazole was determined using B. subtilis W23. A direct relationship exists between cell mass and the concentration of the inhibitor since the extent of inhibition was diminished as the cell mass of the inoculum was increased. Thus, a critical number of molecules must react with the cell to produce inhibition. Experiments were conducted to determine if $Mg^{++}$, which is an important component of cell membranes, affected the inhibition. Cells of B. subtilis W23 were exposed to $10^{-3}$M $MgCl_2$ simultaneously with the test compound or for as long as 15 minutes prior to addition of the hydroxybenzindazole. Growth studies indicated that $Mg^{++}$ did not influence the inhibition when added at either time, establishing that the test compound did not interfere with the $Mg^{++}$ interaction and function in the membrane.

Although the hydroxybenzindazole did not influence the growth of P. fluorescens NND, approximately 95% of the cell population lysed (burst) when cells were grown in the presence of the hydroxybenzindazole. The extent of lysis (cell rupture) was proportional to the benzindazole concentration. Control cells did not lyse during the experiment. The increased lytic rate was not observed when the benzindazole was added after the cells had reached the maximum stationary phase (10 hours); thus, the compounds must be present during active growth for the cells to show the lytic response. These results suggest the compound changes the "architectural configuration" of the cell creating a more fragile structure which bursts; thus the cell is completely destroyed. This is extremely important in controlling or destroying growth of undesirable cells since if the cells rupture they cannot possibly grow and divide at any future time.

Several antibiotics act at the cell surface. The antimicrobial activity of the hydroxybenzindazole in combination with selected antibiotics was measured. The hydroxybenzindazole and penicillin, when tested separately, produced a very slight inhibition of growth. However, a combination of the benzindazole and penicillin showed a pronounced inhibition in the growth of B. subtilis W23.

Similar potentiation was obtained when the hydroxybenzindazole was used in combination with either polymyxin (5 µg/ml) or circulin (30 µg/ml). Both Polymyxin (Pfizer, Inc.) and Circulin (Upjohn Co.) are surface active compounds thought to cause disorganization of the cell membrane leading to a loss of intracellular components. The enhanced antimicrobial activity observed with the combination of hydroxybenzindazole and antibiotics denotes a more pronounced distortion in the cell surface. Thus, much lower concentrations of the compounds can be used in medicinal applications providing an opportunity for toxic compounds to have greater medicinal applicability and use.

The enhanced inhibition was not observed when the hydroxybenzindazole was used in combination with chloramphenicol. Failure of the mixture of hydroxybenzindazole and chloramphenicol to show an enhanced inhibition of growth could be correlated with the internal site of action of chloramphenicol, which is blockage of the binding of the 30s and 50s ribosomal subunits. While the benzindazole does not alter the cell permeability, at least to chloramphenicol, it may distort the integrity of the outer cell structure and thus facilitate or complement the action of the surface active compounds.

Quantitative studies revealed that when cells were incubated with 20 µg of the hydroxybenzindazole approximately 1 µg was bound or adsorbed to the cell. The hydroxybenzindazole (60 µg/ml) did not inhibit uptake or incorporation of L-serine-3-$^{14}$C or uracil-2-$^{14}$C which augments the findings obtained with chloramphenicol sensitivity with its intracellular site of action. Addition of the hydroxybenzindazole to osmoplasts (osmotically sensitive cells) of B. subtilis W23, stabilized in 0.35 M sucrose, did not produce lysis. Failure of the benzindazole to alter uptake of the amino acid and purine base or to facilitate lysis of osmotically sensitive structures, suggests that the compound produces conformational changes in the membrane, but these changes do not results in a loss of cellular integrity with subsequent lysis. Thus the compound can be used to destroy undesirable cells without damaging normal cells.

Inhibition studies using the microorganism B. subtilis W23 indicated that compounds 4 and 7 completely inhibited the growth of the organism. The results indicate that compounds 4 and 7 are biologically active and are potential antibacterial agents.

Members of this class of compounds also inhibit growth of human and mouse cells. For example, growth of both the human tumor KB* and the mouse L-M** cell lines was inhibited when the cells were grown in media containing µg/ml or greater concentrations of either compound 5c or 5d indicating their potential function as anticancer agents. Cultures containing 1µg/ml of either compound 5c or 5d had the same growth rate as the control. During the first 2 days of growth, 10 µg/ml of either compound reduced the growth by 25 to 50 percent. By the fourth day cultures containing 10 µg/ml compound 5c remained at 50% of the control while cultures containing compound 5d showed only a 30% reduction in growth as compared to the control. Increasing the concentration of compound 5d to 20 µg/ml depressed the growth rate only slightly over the rate observed with 10 µg/ml. However, when the concentration of compound 5c was increased to 20 µg/ml, a marked inhibition was observed with no significant increase in cell numbers after three days. The low concentrations required for inhibition establish these compounds as potent inhibitors— probably among the top 5% of compounds presently in use.

---

*The KB cell line was derived from an epidermoid carcinoma in the mouth of an adult male caucasian in December, 1954, by H. Eagle (Proc. Soc. Exp. Biol. Med., 89:362,1955). It was one of the early successful attempts to isolate and serially propagate a human cell line directly in monolayer culture on glass. The line was isolated in a medium consisting of basal medium (Eagle), 90%; human serum, 10%; and in the course of 350 subsequent passages has been adapted to 5% calf serum.

**The L-M strain was derived from NCTC clone 929 (see CCL 1) by R. J. Kuchler and D. J. Merchant during the course of studies on its nutritional requirements (Proc. Soc. Exp. Biol. Med., 92:803, 1956; Exp. Cell Res., 17:490, 1958). L-M is characterized by its propagation in a serum-free medium (Morgan, Morton, and Parker's medium 199 with Bacto-peptone 0.5% or 2X Eagle amino acids and vitamins; Proc. Soc. Exp. Biol. Med., 110:194, 1962), and by marker chromosomes (J. Nat. Cancer Inst., 26:1075, 1961).

To ascertain if the potency of compound 5d was reduced during the incubation in the growth medium in the absence of cells, compound 5d (20 μg/ml) was added to the medium and incubated at 37° C on a shaker for 4 days. Cells ($1 \times 10^5$/ml) were added to the "incubated" compound-containing medium. The inhibition pattern obtained from the "incubated" medium was identical to that obtained when compound 5d (20 μg/ml) was added simultaneously with the inoculation. These results show that detoxification of the compound by either auto-oxidation or enzymatic processes associated with the serum does not occur during continued incubation in the culture medium. Since the compounds are not inactivated by serum, their effectiveness for animal use or human tests is enhanced. This fact is stressed in animal studies recited in Example IX below.

EXAMPLE VIII

The KB cells were plated in plastic tissue culture dishes and grown in a 5% $CO_2$ gas phase incubator for 7 days. The medium was removed, the plates washed with Hanks' salt solution and the cells stained with a 0.5% aqueous crystal violet solution, rinsed and dried. The colonies were counted and the relative plating efficiency calculated using the number of control colonies as 100 percent. The effect of compounds 5c and 5d on KB cell growth is shown in Table I below:

TABLE I

| | Relative plating efficiency (%) Test compound concentration μg/ml | | | |
|---|---|---|---|---|
| Treatment | 0 | 1 | 10 | 20 |
| None | 100 | | | |
| Compound 5c | — | 91 | 38 | 17 |
| Compound 5d | — | 97 | 82 | 79 |

The greater sensitivity of L-M cells to compound 5c was also evident with KB monolayer cultures (Table 1). The colony formation of KB cells (7 days cultures) showed a 38% (62% of the cells were killed) relative plating efficiency in the presence of 10 μg/ml of compound 5c and a 17% relative plating efficiency (83% of the cells were killed) when 20 μg/ml of compound 5c was added to the growth medium. In contrast, compound 5d produced only a very slight inhibition of growth when compared with the control culture, with no significant difference observed between the 10 and 20 μg/ml concentrations. As with L-M cells 1 μg/ml of either compound 5c or compound 5d had little effect on the relative plating efficiency.

EXAMPLE IX

Antitumor Activity of Compound 11a and Antinomycin D in mice.

The test system utilized involved Swiss albino CD-1 female mice weighing 25–27 grams which were injected (i.p.) with $1 \times 10^6$ viable sarcoma 180 ascitis cells. Chemotherapy was initiated 24 hours post-injection with a protocol of five intra-peritonaeal injections at 24 hour intervals.

| Animal Test Groups | Test Regime | |
|---|---|---|
| | Compounds | Quantity Injected |
| 1 | actinimycin D | 4 μg/injection - total 20 μg |
| 2 | compound 11a | 0.8 μg/injection - total 4 μg |
| 3 | actinomycin D plus compound 11a | 4 μg/injection and 0.8 μg/injection |
| 4 | saline | 0.2 ml/injection |

Animals were weighted at 24 hour intervals and the survival time recorded for each test group.

| Results - Test to Control Survival Ratios | Survival time of the test animal (T/C) / Survival time of the control animal |
|---|---|
| Saline | 1.0 |
| Compound 11a | 1.0 |
| Actinomycin D | 1.9 |
| Compound 11a plus Actinomycin D | 4.3 |

(National Institutes of Health guide lines indicate that compounds or combination chemotherapy agents having a T/C ratio greater than 1.25 in the mouse tumor system are of potential use, Cancer Chemotherapy Reports, No. 25, Dec. 1962). The life span of mice with the sarcoma tumor is significantly prolonged by treatment with a combination of the test compound 11a and antinomycin D(T/C = 4.3) establishing an enhancement of anticancer activity by the test material.

COLONY AND CELL MORPHOLOGY

KB cells exposed to 10 and 20 μg/ml of compound 5c did not divide, or if limited division occurred, only a few small colonies were formed containing a small number of cells. Differences in cell morphology were also observed. In contrast to the control, the nuclei of treated cells were located at the periphery of the cell which contained little cytoplasm. In addition, treated cells had a less uniform density with areas of heavy and light staining. Since the difference in staining density could be the result of modification of intracellular structures, such as lysosomes, experiments were performed to determine the effect of the compounds on the permeability of lysosomal membrane.

EXAMPLE X

Relative Acid Phosphatase Staining of KB and L-M Cells Grown in the Presence and Absence of Compound 5c and Compound 5d.

KB and L-M cells were grown on coverslips in medium 199 with 10% calf serum for the 24 hour growth prior to staining in the presence or absence of compound 5c (20 μg/ml) or compound 5d (20 μg/ml). The cells were washed in Hanks' salt solution, incubated at 37° C in Gomori's substrate solution for 1, 2, or 3 hours, washed, treated with a 1% solution of ammonium sulfide, washed, mounted and observed microscopically. Light staining was designated as cells showing only a few scattered granules; medium staining was more dense but distinct isolated granules were still detected; and heavy staining a more intense staining with fewer discrete granules. Heavy staining denotes increased phosphatase activity.

TABLE 2

| Incubation time in substrate (Hours) | Treatment | | |
|---|---|---|---|
| | none | compound 5c | compound 5d |
| 1 | none | light | none |
| 2 | light | medium | light |
| 3 | medium | heavy | medium |

EFFECT ON PERMEABILITY OF LYOSOMAL MEMBRANES

The acid phosphatase activity was measured in KB and L-M cells grown in medium in the presence or absence compound 5c or 5d (20 μg/ml) for 2 or 24 hours prior to staining (Table 2). Quantitative evaluation of the relative staining intensity of the lysosomes was compared in the treated and untreated cells. The staining intensity of the cells treated for 2 hours was indistinguishable from untreated cells. However, differences were noted for cells grown for 24 hours. Cells grown in the presence of compound 5c showed light staining after 1 hour incubation in the substrate while the control and compound 5d treated cells did not stain. For all three substrate incubation times, the control and compound 5d treated cells showed identical staining reactions while compound 5c treated cells showed a more intense staining reaction. Thus, cells grown in the presence of compound 5c accumulate the phosphatase substrate within the lysosomes much more rapidly than the control or compound 5d treated cells indicating the compounds ability to alter membrane permeability and thus regulate the accumulation of essential metabolites. Control of this cellular capacity permits regulation of cell division so important in cancer chemotherapy. Since the permeation of the substrate is the rate-limiting step in the phosphatase determination, compound 5c produces a modification of the lysosomal membrane which increased the permeability of the lysosome to the substrate. The results also emphasize the difference in biological activity of compound 5c and 5d type molecules which chemically are similar except at C-3. Differences in the biological activity have been observed when the compounds were tested using various bacteria. In experiments not shown, the treatment of cells with Triton X-100 (octyl phenoxypolyethoxyethanol) which is known to alter cell permeability resulted in the same final staining intensity as growth in the presence of compound 5c. Thus, this control experiment indicated compound 5c does not induce synthesis of acid phosphatase in the cell but does alter cell permeability.

EXAMPLE XI

Effect of Compound 5c (15 μg/ml) on Uptake and Incorporation of $^3$H-Thymidine, $^3$H-Uridine and $^{14}$C-Leucine by L-M Cells.

$^3$H-Thymidine (10 μCi), or $^3$H-uridine (10 μCi), or $^{14}$C-leucine (5 μCi), was added to suspension cultures of L-M cells ($8 \times 10^5$; /ml) in McCoy's 5a modified medium containing either 0 or 15 μg/ml of compound 5c. The cells were incubated at 37° C. One ml samples were removed at varying intervals and the rates of uptake and incorporation were determined from the liner portion of radioactivity versus time curves.

TABLE 3

| Substrate | Addition | Rate Cpm/8×10$^5$ cells/hr | | Cell Pool |
|---|---|---|---|---|
| | | Uptake | Incorporation | |
| $^3$H-thymidine | none | 4,200 | 3,000 | 1,200 |
| | compound 5c | 2,000 | 1,300 | 700 |
| $^3$H-uridine | none | 8,400 | 4,000 | 4,400 |
| | compound 5c | 3,000 | 1,400 | 1,600 |
| $^{14}$C-leucine | none | 9,600 | 6,000 | 3,600 |
| | compound 5c | 4,000 | 2,800 | 1,200 |

EFFECT ON UPTAKE AND INCORPORATION

The uptake of radioactive thymidine, uridine, and leucine, precursors for DNA, RNA and protein, respectively, was inhibited when suspension cultures of L-M cells were incubated in the presence of 15 μg/ml of compound 5c (Table 3). The radioactivity present in the pool for each of the precursors was reduced by about 66% showing that the inhibition was not substrate specific but that all substrates were inhibited, and the decreased pool levels could account for the decreased incorporation into the macromolecules that was observed. These results augment the previous findings that regulation (inhibition) of the ability of cells to accumulate essential metabolites (food) by these compounds makes them excellent anticellular agents. To further stress the importance of the compounds these results also indicate an inhibition of synthesis of DNA (nuclear material), RNA and proteins which is essential to controlling cell growth and division, especially in malignant cells.

THE EFFECTS OF THE AZASTEROIDS ON TESTIS FUNCTION

The compounds as shown in Table 7 were dissolved in a minimal amount of ethanol and diluted in sesame oil (1 mg/ml). After dilution, samples were stored at 5° C in the dark and flushed with N$_2$ every 24 hours. The compounds were injected subcutaneously into adult male mice for a period of 10 days. Each mouse injected received a total dose of 2 mg over the 10 day period or 0.2 mg per day. The mice were random bred males of the ICR-Swiss strain and were used in the study when they reached 75±2 days of age. Mice were maintained in air-conditioned and light-controlled (14 hour light/24 hour) animal quarters and provided with lab food and water ad libitum. Animals were necropsied 24 hours after the last injection. Testes and seminal vesicles were excised, trimmed of adhering tissue and weighed fresh at the nearest one-tenth milligram. The results of the weight studies are shown in Table 4. No significant changes in the testes weight or total body weight were noted indicating the compounds do not produce adverse effects in animals, which is very important if compounds are to be used in human medicinal programs.

TABLE 4

Average Body, Testis and Seminal Vesicle Weight After Treatment with Various Azasteroids

| Compound Number | No. of Mice Treated | Body Weight (g) | Testes Paired Testes (mg) | Testes Mg Testes Per g Body Wt. | Seminal Vesicle (mg) |
|---|---|---|---|---|---|
| 4c | 2 | 35.7 | 261.0 | 7.28 | 82.1 |
| 2 | 4 | 35.7 | 242.0 | 6.73 | 87.3 |
| 5d | 5 | 32.3 | 201.6 | 6.32 | 67.7 |
| 5g | 5 | 34.3 | 178.0 | 5.20 | 97.0 |
| 11B | 2 | 34.0 | 229.0 | 6.67 | 88.7 |
| Sesame Oil alone | 5 | 34.0 | 223.5 | 7.35 | 80.1 |

IN VITRO TESTIS METABOLISM STUDIES

For these investigations the compounds were diluted in a minimal amount of ethanol and further diluted in saline (0.85%) so that the final concentration was 1 mg/ml. The compounds were placed in solution and gassed under $N_2$ and stored at 5° C until used 2 days later for the in vitro incubation studies. Details of the in vitro incubation procedures may be found in *Endocrinology* 89:791–800 (1971).

The effects of these compounds on glucose oxidation by testis tubules was examined by incubating about 200 mg of teased testis tubules from mature rats in a 25 ml Erlenmeyer flask containing 3 ml of Krebs Ringer bicarbonate buffer (pH 7.4), D-glucose-U-$^{14}$C (0.5 µCi; 10mM) and 0.25 ml of the azasteroid (1 mg/ml) to be tested. The flasks were incubated for 2 hours at 33° C under 95% $O_2$:5% $CO_2$. The reaction was terminated by adding 0.25 ml of 5 N $H_2SO_4$. Carbon dioxide was trapped in 0.25 ml of hydroxide of Hyamine. The radioactivity present in the Hyamine was determined by liquid scintillation spectrometry. The results of this study are summarized in Table 5. This table includes a detailed summary of the results obtained and an average for each compound. In this assay compounds 2, 5c and 5d depressed glucose oxidation in vitro more than compounds 4c and 11b. The latter compounds were comparable to saline. Reduction of oxidative potential, so important in sperm development, suggests interference with spermatogenesis indicating action as antifertility agents. These results were confirmed by sperm counts and failure of female mice to conceive when placed with males treated with these compounds. Thus, the compounds have potential for antifertility activity in the control of wild rodent populations and possibly stray animals such as dogs and cats.

TABLE 5

EFFECT OF COMPOUNDS ON GLUCOSE OXIDATION (GLUCOSE-U-$^{14}$C) BY RAT TESTIS TUBULES

| FLASK NUMBER | COMPOUND NUMBER TESTED | TISSUE TISSUE + TARE | WEIGHT TARE | (mg) ACTUAL WEIGHT TISSUE | GLUCOSE OXIDATION CPM/FLASK | GLUCOSE OXIDATION CPM/100 mg |
|---|---|---|---|---|---|---|
| 1 | Saline | 463.43 | 261.67 | 201.7 | 23,441 | 11,621 |
| 2 | 4c | 464.17 | 268.04 | 196.13 | 17,350 | 8,847 |
| 3 | 2 | 476.41 | 271.44 | 205.0 | 6,876 | 3,354 |
| 4 | 5d | 473.60 | 273.40 | 200.2 | 32,194 | 16,081 |
| 5 | 5c | 479.11 | 273.19 | 205.9 | 12,450 | 6,046 |
| 6 | 11b | 479.58 | 276.23 | 203.3 | 23,529 | 11,590 |
| 7 | Saline | 482.49 | 276.30 | 206.2 | 21,645 | 10,497 |
| 8 | | 480.20 | 277.31 | 203.0 | 19,930 | 9,817 |
| 9 | 4c | 481.02 | 278.74 | 202.3 | 17,325 | 8,564 |
| 10 | 2 | 483.27 | 277.55 | 205.7 | 8,557 | 4,159 |
| 11 | 5d | 479.73 | 278.06 | 201.7 | 16,539 | 8,200 |
| 12 | 5c | 483.71 | 279.87 | 203.8 | 21,027 | 10,317 |
| 13 | 11b | 483.71 | 278.93 | 204.8 | 15,382 | 7,510 |
| 14 | Saline | 493.03 | 278.22 | 214 | 19,680 | 9,196 |

| COMPOUND NUMBER | AVERAGE CPM/100 mg TISSUE | % DEVIATION FROM CONTROL |
|---|---|---|
| Saline | 10,719 | 0.0% |
| 4c | 8,705 | −19.94% |
| 2 | 3,756 | −63.6% |
| 5d | 12,140 | +17.4% |
| 5c | 8,181 | +20.8% |
| 11b | 9,550 | |
| Saline | 9,946 | |

Legend:
CPM = counts per minute. Glucose-U-$^{14}$C activity was 0.5 millicurie. All compounds were tested in a concentration of 250 mg per flask.

The effects of the compounds on the incorporation of lysine -U-$^{14}$C into trichloroacetic (TCA) precipitable protein of rat testes was investigated by incubating about 200 mg of teased testis tubules from mature rats in a 25 ml Erlenmeyer flask containing 3 ml of Krebs Ringer bicarbonate buffer (pH 7.4), L-lysine-U-$^{14}$C (0.5 μCi; 0.1mM), glucose (10 mM) and 0.25 ml of the azasteroid to be tested. The flasks were incubated for 1 hour at 33° C under 95% $O_2$: 5% $CO_2$ and the TCA precipitable protein was isolated and an aliquot used to measure radioactivity. The results shown in TABLE 6 indicate that compounds 2, 4c, 5d and 11b depress protein synthesis by teased testis tubules. The incorporation of $^{14}$C into TCA precipitable material in the presence of compound 5c was similar to the saline control.

TABLE 6

EFFECT OF COMPOUNDS ON LYSINE INCORPORATION INTO PROTEIN BY RAT TESTIS TUBULES

| FLASK NUMBER | COMPOUND NUMBER TESTED | TISSUE WEIGHT (mg) | | | CPM/FLASK | CPM/100 mg |
| --- | --- | --- | --- | --- | --- | --- |
| | | TARE + TISSUE | TARE ALONE | ACTUAL WEIGHT TISSUE | | |
| 17 | Saline | 461.48 | 259.11 | 202.37 | 3,750 | 1,852 |
| 19 | 4c | 459.81 | 263.05 | 196.76 | 2,575 | 1,309 |
| 20 | 2 | 464.41 | 264.51 | 199.90 | 2,000 | 1,000 |
| 21 | 5d | 468.87 | 265.47 | 203.4 | 3,225 | 1,585 |
| 22 | 5c | 472.62 | 266.90 | 205.72 | 3,325 | 1,616 |
| 23 | 11b | 461.71 | 266.93 | 194.78 | 2,325 | 1,194 |
| 25 | Saline | 473.12 | 271.47 | 201.65 | 3,550 | 1,761 |
| 27 | 4c | 473.18 | 274.19 | 199.00 | 2,925 | 1,470 |
| 28 | 2 | 467.78 | 277.03 | 190.73 | 1,200 | 629 |
| 29 | 5d | 459.19 | 257.07 | 202.12 | 3,125 | 1,546 |
| 30 | 5c | 465.61 | 264.30 | 201.31 | 4,575 | 2,273 |
| 31 | 11b | 468.25 | 268.91 | 199.34 | 2,225 | 1,116 |

| COMPOUND NUMBER | AVERAGE OF TWO FLASK CPM/100 mg tissue |
| --- | --- |
| 4c | 1,389 |
| 2 | 814 |
| 5d | 1,565 |
| 5c | 1,944 |
| 11b | 1,155 |
| Saline | 1,806 |

Legend:
CPM = counts per minute. All compounds were tested in a concentration of 250 mg per flask.

TABLE 7

Amounts of compounds used for antifertility testing.
Compound 4c: 4.73 mg.
Compound 2: 8.61 mg.
Compound 5d: 19.18 mg.
Compound 5c: 21.36 mg.
Compound 11b: 4.61 mg.

It will appear from an examination of the evaluation of the compounds that sharp biological effects are achieved at exceeding low concentrations. The compounds are essentially analogs of estrone and equilenin and all are characterized by solubility in water. The low concentrations greatly enhance the potential use of these test compounds in human experimentation. At these levels the compounds are very active and no adverse effects have been observed in our experimentation.

The methods of preparation set forth herein are by way of example and variations and alternative methods may be obvious to those skilled in the art, all within keeping with the spirit and scope of this disclosure. The new compounds disclosed herein include the optical isomers thereof.

What is claimed:

1. A compound of the formula:

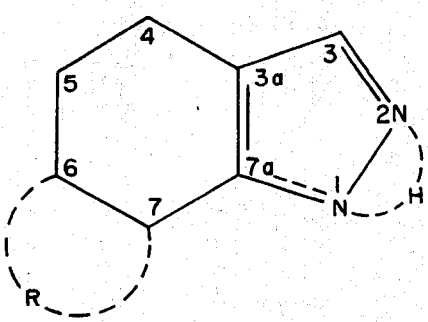

wherein R represents the carbon and hydrogen atoms necessary to complete one of the following structures:

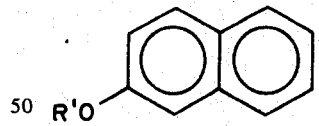

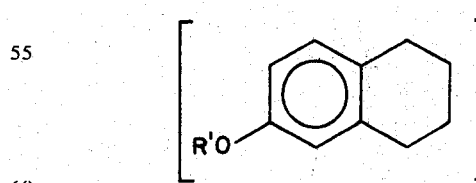

or

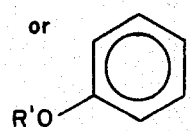

in which R' is a member selected from the group consisting of H, CH$_3$, bridgehead carbon atom 3a is unsubstituted or substituted by H or CH$_3$ in which case the only double bond in the pyrazole ring is represented by the dashed line and two valences of carbon 3 are satisfied by two hydrogen atoms and H is a labile hydrogen atom attached to one of two nitrogen atoms, said oxygen being attached to carbon 3 only when said labile hydrogen atom is attached to nitrogen number 2 of the pyrazole ring.

2. A compound of the formula:

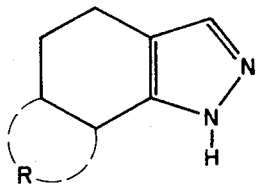

wherein the substituent R is the same as in claim 1.

3. A compound of the formula:

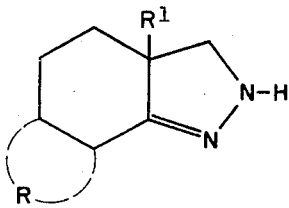

wherein the substituent R is the same as in claim 1 and R$^1$ is a member selected from the group consisting of H and CH$_3$.

4. 10,11-Dihydro-7-methoxy-3H-naphthindazole.
5. 10,11-Dihydro-3H-naphthindazol-7-ol.
6. 4,5-Dihydro-1H-benz-7-ol.

* * * * *